(12) United States Patent
Sheskey et al.

(10) Patent No.: US 7,070,828 B2
(45) Date of Patent: Jul. 4, 2006

(54) PROCESS FOR COATING SOLID PARTICLES

(75) Inventors: Paul J. Sheskey, Midland, MI (US); Colin M. Keary, Midland, MI (US)

(73) Assignee: Dow Global Technologies, Inc., Midland, MI (US)

( * ) Notice: Subject to any disclaimer, the term of this patent is extended or adjusted under 35 U.S.C. 154(b) by 0 days.

(21) Appl. No.: 10/484,325

(22) PCT Filed: Aug. 23, 2002

(86) PCT No.: PCT/US02/26764

§ 371 (c)(1), (2), (4) Date: Jun. 21, 2004

(87) PCT Pub. No.: WO03/020247

PCT Pub. Date: Mar. 13, 2003

(65) Prior Publication Data

US 2004/0234676 A1  Nov. 25, 2004

Related U.S. Application Data

(60) Provisional application No. 60/317,402, filed on Sep. 4, 2001.

(51) Int. Cl.
*B05D 5/00* (2006.01)

(52) U.S. Cl. .................. 427/2.14; 427/213.3; 427/242

(58) Field of Classification Search ................. 427/2.1, 427/2.14, 212, 213.3, 213.35, 242, 421, 426
See application file for complete search history.

(56) References Cited

U.S. PATENT DOCUMENTS

| | | | |
|---|---|---|---|
| 3,431,138 A | 3/1969 | Zingerman et al. | 117/100 |
| 3,607,364 A | 9/1971 | Lopez et al. | 117/100 |
| 4,152,078 A | 5/1979 | Pilgrim | 366/144 |
| 4,476,145 A | 10/1984 | Hardie-Muncy et al. | 426/285 |

(Continued)

FOREIGN PATENT DOCUMENTS

| | | |
|---|---|---|
| DE | 19910789 | 9/2000 |
| EP | 0 504 870 | 9/1992 |
| EP | 1 120 109 | 8/2001 |
| GB | 2 355 008 | 4/2001 |

OTHER PUBLICATIONS

J. Appl. Chem. 1, 425-429 (1951). "A mechanical foam generator for use in labortories". J.F. Fry & R.J. French.

(Continued)

Primary Examiner—Jennifer Michener

(57) ABSTRACT

A process for coating solid particles which comprises the steps of a) contacting a gas with a fluid composition comprising i) a polymer and ii) a liquid diluent to produce a foam, and b) contacting the produced foam with solid particles and agitating the particles to provide a coating on the solid particles.

17 Claims, 1 Drawing Sheet

U.S. PATENT DOCUMENTS

Figure 1:
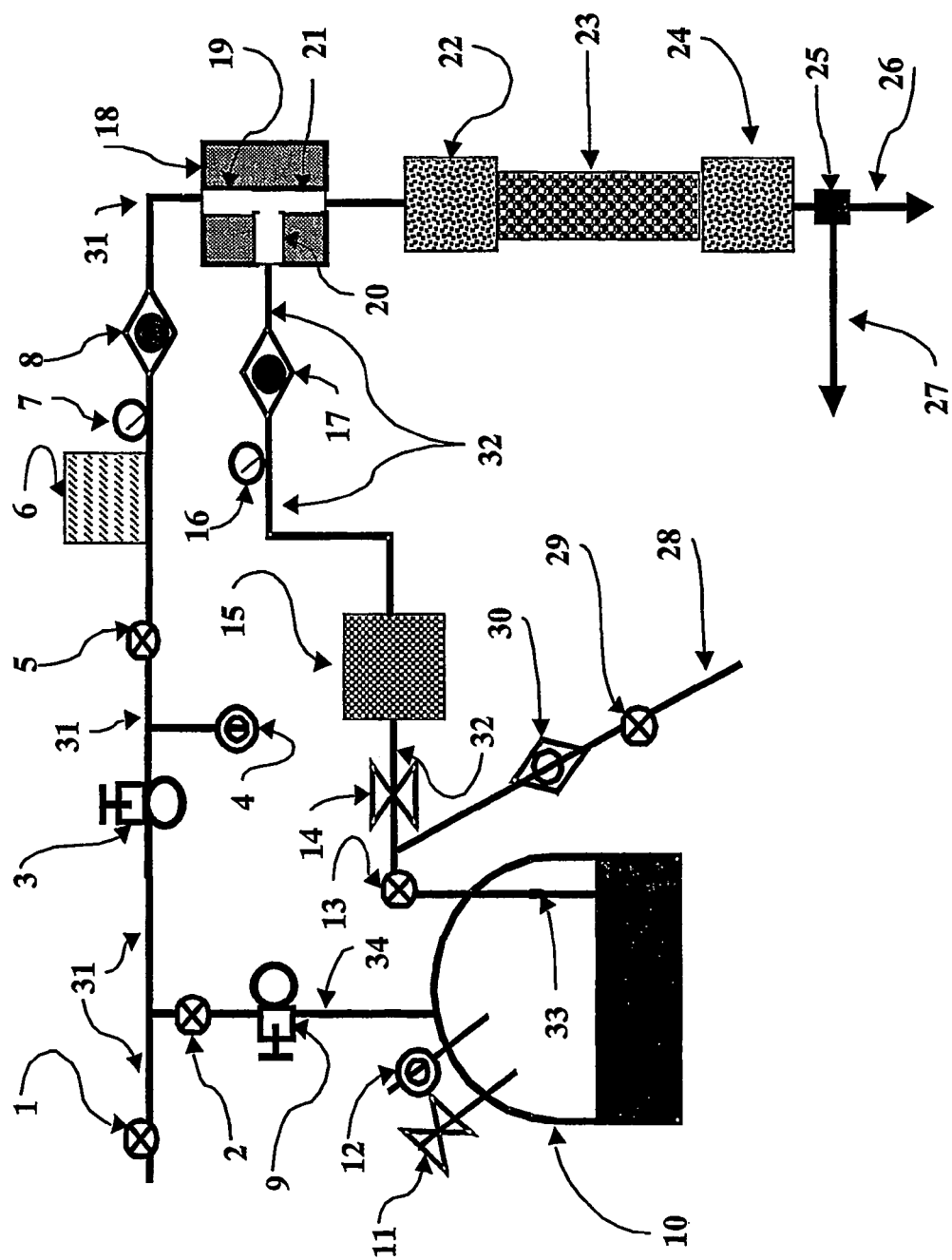

| | | | |
|---|---|---|---|
| 4,645,812 A | 2/1987 | Maier | 526/200 |
| 4,965,089 A | 10/1990 | Sauter et al. | 427/3 |
| 5,026,735 A | 6/1991 | Stern | 521/50 |
| 5,641,536 A * | 6/1997 | Lech et al. | 427/2.14 |
| 6,280,515 B1 | 8/2001 | Lydzinski et al. | 106/122 |

OTHER PUBLICATIONS

Patent Abstract vol. 12, No. 176 (C-498) & JP 62-283919A, Dec. 1987 ; Roller Japan KK, Sustained-release tablets—include foaming layer enabling tablet to float when in contact with gastric juice.

* cited by examiner

PROCESS FOR COATING SOLID PARTICLES

This application claims the benefit of provisional application No. 60/317,402 filed Sep. 4, 2001.

This invention relates to a process for coating solid particles, particularly drug-containing solid particles, such as pharmaceutical tablets, granules and pellets.

BACKGROUND OF THE INVENTION

Coatings are generally applied to solid particles, such as pharmaceutical forms, to protect the ingredients against the atmosphere, to mask unpleasant tastes and odors, to ease in swallowing, to improve the appearance as well as providing coloring and printing.

Methylcellulose and hydroxypropyl methylcellulose have been used for a long time as coating materials for pharmaceutical forms. U.S. Pat. No. 3,431,138 discloses that these coating are tacky, uneven, and require extensive polishing after coating. To solve these problems, the U.S. Patent suggests a coating composition which comprises from 50 to 60 weight percent of ethanol, from 35 to 45 weight percent of chloroform and from 2 to 5 weight percent of low viscosity methyl cellulose. Since the issue of the U.S. patent, the coating technology has progressed and high quality coatings are obtainable without the use of chloroform. Nowadays methylcellulose and hydroxypropyl methylcellulose are dissolved in water or a mixture of water and alcohol and sprayed on an agitated mass of pharmaceutical forms. The spraying technique is a sophisticated process which requires well-defined processing parameters and quite complex equipment Moreover, the viscosity of the solutions of methylcellulose and hydroxypropyl methylcellulose must be low enough that they are still sprayable.

U.S. Pat. No. 3,607,364 discusses in detail the disadvantages of spray coating of pharmaceutical solid forms, such as the high pressures which are required to sufficiently atomize a coating medium. To solve these problems, U.S. Pat. No. 3,607,364 discloses a process for coating a pharmaceutical solid form wherein a foamed viscous sugar medium is applied to the solid surface, the coating medium is then urged against the solid form surface to break down the foam and produce an even coat of the coating medium on the solid form surface. Unfortunately, the examples reveal that this method requires a lot of work and time. 15 to 20 coats were required to obtain elegant coated tablets.

U.S. Pat. No. 4,965,089 relates to a method and apparatus for coating caplets with gelatin. There are two primary methods of applying a liquid gelatin composition to a pill. The first method is to hold the pill or tablet during a dipping process. Unfortunately, quite sophisticated and expensive equipment is necessary to provide an inefficient dipping process that suffers from long processing times and product variability. The second method is to spray a coating over the pill as it tumbles.

In view of the deficiencies of the prior art processes, it is an object of the present invention to provide a new process for coating solid particles.

SUMMARY OF THE INVENTION

The present invention relates to a process for coating solid particles which comprises the steps of
a) contacting a gas with a fluid composition comprising i) a polymer and ii) a liquid diluent to produce a foam, and
b) contacting the produced foam with solid particles and agitating the particles to provide a coating on the solid particles.

SHORT DESCRIPTION OF THE DRAWING

FIG. 1 illustrates a foam generating device for producing foam in step a) of the process of the present invention.

DETAILED DESCRIPTION OF THE INVENTION

As a starting material for step a) of the process of the present invention a fluid composition is prepared which comprises i) a polymer, ii) a liquid diluent and optionally iii) one or more additives which provide robustness or aesthetics to the finished article. The fluid composition may comprise one or more different polymers. A wide range of polymers is useful. Hydrophilic polymers are preferred. Examples of naturally occurring polymers include gum arabic, xanthan gum, gum karaya, gum tragacanth, gum ghatti, guar gum, exudate gums, seaweed gums, seed gums, microbial gums, carrageenan, dextran, gelatin, alginates, pectins, starches, polysaccharides, such as cellulose ethers or cellulose esters, starch derivatives, guar derivatives or xanthan derivatives. Starch derivatives, guar derivatives or xanthan derivatives are described in more detail in European patent EP 0 504 870 B, page 3, lines 25–56 and page 4, lines 1–30. Useful starch derivatives are for example starch ethers, such as hydroxypropyl starch or carboxymethyl starch. Useful guar derivatives are for example carboxymethyl guar, hydroxypropyl guar, carboxymethyl hydroxypropyl guar or cationized guar. Preferred hydroxypropyl guars and the production thereof is described in U.S. Pat. No. 4,645,812, columns 4–6.

Other examples of useful polymers are homo- or copolymers of ethylene imine, an unsaturated acid, such as acrylic acid or a salt thereof, an unsaturated amide, such as acrylamide, a vinyl polymer, such as vinylalcohol, a vinyl ester, such as vinylacetate, vinylpyrrolidone, vinyloxazolidone, vinylmethyloxazolidone, ethylene sulfonic acid, vinylamine, vinylpyrridine, an alkylglycol, a polyalkylene oxide, such as polyethylene oxide, or an oxyethylene alkylether.

Preferred polymers are cellulose esters or cellulose ethers. Preferred cellulose esters are carboxy-$C_1$–$C_3$-alkyl celluloses, such as carboxymethyl celluloses, or carboxy-$C_1$–$C_3$-alkyl hydroxy-$C_1$–$C_3$-alkyl celluloses, such as carboxymethyl hydroxyethyl celluloses. Preferably, the cellulose ethers are $C_1$–$C_3$-alyl celluloses, such as methylcelluloses; $C_1$–$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$–$C_3$-alkyl celluloses, such as hydroxyethyl hydroxypropyl celluloses; or alkoxy hydroxyethyl hydroxypropyl celluloses, the alkoxy group being straight-chain or branched and containing 2 to 8 carbon atoms. Most preferably, the fluid composition comprises a water-soluble cellulose ether, such as a methylcellulose with a methyl molar substitution $DS_{methloxyl}$ of from 0.5 to 3.0, preferably from 1 to 2.5, or a hydroxypropyl methylcellulose with a $DS_{methoxyl}$ of from 0.5 to 3.0, preferably from 1 to 2.5 and a $MS_{hydroxypropoxyl}$ of from 0.05 to 2.0, preferably from 0.1 to 1.5. The viscosity of the cellulose ether generally is from 1 to 100,000 mPa·s, preferably from 3 to 10,000 mPa·s, more preferably from 3 to 5,000 mPa·s, and most preferably from 5 to 200 mPa·s measured as a 2-wt. % aqueous solution at 20° C. using an Ubbelohde viscometer.

Preferably, the polymers i) are non-crosslinked. Preferably polymer i) forms a self-supporting, coherent film if the polymer i) is in its undiluted stage.

The polymer i) generally has a weight average molecular weight of at least 10,000, preferably at least 12,000, more preferably at least 15,000, most preferably at least 18,000. The preferred upper limit for the weight average molecular weight largely depends on the type of polymer. Generally the weight average molecular weight of the polymer i) is up to 5,000,000, preferably up to 500,000, more preferably up to 100,000.

The term "liquid diluent" means a diluent that is liquid at normal pressure and 25° C. The liquid diluent preferably is a monomeric compound or an oligomeric compound with a molecular weight of up to 500, preferably up to 300. Useful organic liquids are alcohols, preferably monofunctional alcohols, such as ethanol; alkenes, alkanes, halogenated alkenes, halogenated alkanes, ethers, esters or oils, such as paraffin oils, animal oils or vegetable oils. Most preferably, the liquid diluent is water.

The fluid composition used in step a) of the present invention generally comprises from 0.01 to 30 percent, preferably from 0.1 to 20 percent, more preferably from 0.5 to 15 percent, and most preferably from 1 to 5 percent of the polymer i) and from 99.99 to 70 percent, preferably from 99.9 to 80 percent, more preferably from 99.5 to 85 percent, and most preferably from 99 to 95 percent of the liquid diluent ii), based on the total weight of the polymer i) and the liquid diluent ii).

Generally polymers i) are chosen which have surface-active properties. The above-mentioned polymers, particularly water-soluble cellulose ethers, are useful as a surfactant in a water-based fluid composition used in step a) of the process of the present invention. In some cases it may be useful to include a surfactant other than the polymer i) in the fluid composition. However, in many cases the fluid composition preferably does not comprise a substantial amount of a surfactant other than the polymer i). This means that the fluid composition preferably does not contain a surfactant other than the polymer i) in a sufficient amount to cause foaming of the fluid composition upon contact with a gas. More preferably, the fluid composition does not comprise any amount of a surfactant other than the polymer i). Most preferably, the fluid composition does not comprise a known nonionic, cationic, anionic or amphoteric surfactant, as for example listed in U.S. Pat. No. 5,026,735, column 6, lines 47–68 and column 7, lines 1–22.

The fluid composition may contain one or more additional solid or liquid components such as drugs or one or more additives which provide robustness or aesthetics to the finished article, such as fillers, pigments flavors or plasticizers. If present, their total amount is generally up to 75 percent, preferably up to 50 percent, more preferably up to 25 percent, based on the total weight of the fluid composition. If the fluid composition comprises a cross-linking agent, its amount preferably is not more than 3 percent, more preferably not more than 1.5 percent, most preferably not more than 0.5 weight percent, based on the weight of the polymer i). Most preferably, the fluid composition is free from cross-linking agents.

A two-phase foam may be composed of an aqueous phase and a gaseous phase or a non-aqueous liquid phase and a gaseous phase. A three-phase foam may comprise, in addition to aqueous and gaseous phases, insoluble solids or immiscible liquids. Such three-phase foams can also contain dissolved solids in the aqueous or immiscible liquid phase or in both liquid phases. Four-phase foams may comprise, in addition to aqueous and gaseous phases, immiscible liquids and insoluble solids. In all foams, any immiscible liquid phase may be present as an oil-in-water or water-in-oil emulsion or as a simple dispersion.

The fluid composition is contacted with a gas, such as oxygen, nitrogen, carbon dioxide or, preferably, air to produce a foam. Preferably a water-based air foam is produced. The term "air foam" is used in its industry-accepted sense to mean a foam made by physically mixing air into a fluid, and thus the term is distinct from chemical or carbon dioxide foam or halocarbon blown foam. The foam can be produced in a known manner by mechanically or physically entraining or dispersing the gas in the fluid composition, for example by pumping the fluid composition to air-aspirating, foam producing equipment. The gas and the fluid composition are generally contacted at such amounts to produce a foam with an overrun of 50 to 10,000 percent, preferably from 80 to 2,000 percent, more preferably from 100 to 1,500 percent. The overrun is defined below.

$$\text{Overrun}(\%) = [(\text{volume foam} - \text{volume fluid})/\text{volume fluid}] \times 100.$$

The overrun is measured at 25° C. and atmospheric pressure.

The produced foam comprises a discontinuous gas phase, preferably an air phase, and a continuous fluid phase, preferably an aqueous phase, comprising at least the polymer and bound liquid. Generally the lamella or fluid film of the gas bubbles is viscous due to the presence of the polymer. In case the fluid film comprises a hydrophilic polymer such as a cellulose ether, water is retained in the lamella of the gas bubbles. The drainage of the liquid from the lamellae is minimized, reduced or prevented; such a foam is designated as "non-draining foam" in the art. The foam produced in step a) generally has an average bubble diameter in the range of from about 1 micrometer to about 2,000 micrometers, preferably from about 5 micrometers to about 1,000 micrometers, more preferably from about 10 micrometers to about 300 micrometers. It is to be understood that the measurements of the foam diameter generally are not very accurate in view of the dynamic properties of the foam. It has been found that surprisingly high foam qualities can be achieved, particularly if the polymer i) in fluid compositions used for producing the foam is a cellulose ether. The foam quality FQ is given in percent at atmospheric pressure and 25° C. and is defined as follows:

$$FQ(\%) = [\text{gas volume}/(\text{gas volume} + \text{fluid volume}) \times 100].$$

The foam quality can be measured by measuring the foam volume that is produced from a given volume of fluid at atmospheric pressure and 25° C. In step a) of the process of the present invention generally foams with a foam quality of from 52 to 99.9 percent, preferably from 65 to 99.9 percent, more preferably from 85 to 99 percent are produced. Such high foam quality is surprising for "non-draining foams".

The foam preferably has a measured foam density of up to 0.1 g cm$^3$.

In step b) of the process of the present invention the foam produced in step a) is contacted with solid particles and the particle are agitated to provide a coating on the solid particles. The solid particles preferably have an average diameter of from 0.01 to 100 mm, more preferably from 0.1 to 30 mm, most preferably from 1 to 25 mm. The process of the present invention is particularly useful for coating solid particles containing a drug, that means for solid pharmaceutical forms, preferably tablets, granules, pellets, caplets, capsules, lozenges, suppositories, pessaries and implantable dosage forms. The solid particles may comprise known ingredients, such as pharmaceutical excipients, for example lactose, dicalcium phosphate, microcrystalline cellulose, sugars, minerals, cellulose powder, disintegrants, binders, lubricants, colorants, flavorants or combinations thereof.

The weight ratio between the foam and the solid particles generally is from 1:20 to 1:0.002, preferably from 1:10 to 1:0.01, more preferably from 1:5 to 1:0.1. These ratios may be varied, by those skilled in the art, according to the average particle size of the solids. Preferably, the foam and the solid particles are contacted in such ratios that the amount of the above-mentioned polymer i) is from 0.01 to 20, more preferably from 0.05 to 15, most preferably from 0.075 to 10 percent, based on the weight of the solid particles.

The solid particles are agitated, such as tumbled, dipped through the foam or otherwise moved in coating step b). The agitation of the particles can be started before, during or after the contact of the particles with the foam. However, agitation of the particles is preferably started before the foam is added to the particles and is continued during the foam addition. More preferably, in step b) foam is added to continuously agitated solid particles.

Step b) can be conducted in a known coating device, for example in a tumbler, perforated side-vented coating pan, Wurster column insert in a fluid-bed device, low-shear blender or a continuous coating device of any configuration. Preferably, the foam is added continuously or semi-continuously to the agitated solid particles. The foam can be added to the solid particles by means of a simple tube of which the end is placed closely to or into the mass of solid particles.

According to the process of the present invention a surprisingly smooth coating of constant thickness on the solid particles is achieved. Usually up to 5 coats, in most cases only up to 3 coats, typically even 1 to 2 coats are sufficient to provide a glossy, smooth coating of constant thickness and good gloss. Moreover, a simple device can be used for applying the foam to the solid particles, such as a simple tube. Maintenance-intensive, expensive and complex atomizing devices that are commonly used for spraying fine droplets of liquids on solid particles are not necessary.

Furthermore, it has been found that the process of the present invention is particularly useful for solid particles which are sensitive to mechanical stress, such as tumbling or other movements in the coating apparatus. The foam has a cushioning effect for the solid particles during the coating step b) and, accordingly, helps to decrease the damage of the solid particles during the coating step.

Moreover, the process of the present invention is very versatile and not limited by as many process parameters as coating processes using spraying or atomizing technology of the prior art. For example the process of the present invention it useful for applying non-aqueous and mixed aqueous/non-aqueous coatings, such as flavors, oils or colorants to the solid particles. Moreover, there is no limitation to the viscosity of the applied coating. In contrast to the known spraying technology, highly viscous coatings can be applied to the solid particles according to the process of the present invention. Moreover, in the process of the present invention even fine solid particles can be comprised in the foamed coating composition and can be applied to the particles to be coated without the risk of plugging spray nozzles. Moreover, the process of the present invention is useful for evenly coating a larger variety of particle shapes than with the spraying or atomizing technology of the prior art. Furthermore, by application of foamed compositions comprising blends of immiscible coloring agents multi-color coating can be achieved.

The present invention is further illustrated by the following examples which should not be construed to limit the scope of the present invention. All parts and percentages are by weight unless otherwise indicated. The alkyl and hydroxyalkyl substitutions of the cellulose ethers indicated in the examples below are measured and calculated according to ASTM D3876. The apparent viscosities indicated in the examples below are measured and normalized to a 2 weight percent aqueous solution using an Ubbelohde viscometer at 20° C.

EXAMPLE 1

A) Production of the Tablets to be Coated

Placebo tablets are produced from 20 weight percent of a microcrystalline cellulose, which is commercially available from FMC Corporation under the trademark Avicel PH 102, 79.5 weight percent of fast flow lactose, commercially available from DMV International Pharma and Foremost Farms USA under the designation FFL-316, and 0.5 weight percent of magnesium stearate. The composition is compressed into standard-concave tablets of a diameter of 0.5 inch (13 mm).

B) Production of the Foam

An aqueous dispersion of 5 weight percent of a powder composition in 95 weight percent of water is prepared. The powder composition comprises a hydroxypropyl methyl cellulose and is commercially available under the Trademark Opadry Yellow (06K12172), manufactured by Colorcon (West Point, Pa., USA).

From the aqueous solution a foam is prepared as illustrated in FIG. 1.

Air flows through a tube 31 equipped with ball valves 1, 2 and 5, with pressure regulators and gauge 3 and 9, with a pressure relief valve 4, a mass flow controller 6, a pressure gauge 7 and a check valve 8. The aqueous solution is passed from a pressure vessel 10, which is equipped with a pressure relief valve 12, needle valve 11, air inlet tube 34 and a dip-pipe 33, through a tube 32. Tube 32 is equipped with a ball valve 13, a needle valve 14, an oval gear flow meter 15, a pressure gauge 16 and a check valve 17 and with a water supply line 28, a ball-valve 29 and a check valve 30. The air stream and fluid stream meet in T-piece 18 comprising a air-inlet port 19, a fluid inlet port 20 and a foam outlet port 21. The air stream is dispersed in the water stream by in-line filters 22 and 24 and additionally in packed tube 23 whereby the foam is produced and exits the foam production device via tube 26 or 27 according to the position of 3-way valve 25. The in-line filters used for preparing the foams in the examples have a pore size of 90 micrometers, but generally in-line filters with pore sizes of from 0.5 to 90 micrometers, more preferably from 15 to 90 micrometers are useful for simple foams. For foams containing solids or emulsions, the in-line filters are preferably replaced with strainer elements whose only function is to keep the glass beads in tube 23. Such strainer elements preferably have a nominal pore size of about 440 micrometers. The in-line filters 22 and 24 are connected via a tube 23. The stainless steel tube 23 in the foam production device used in the examples is approximately 25 cm. long by 12.8 cm. external diameter, and is packed with glass beads of 3 mm diameter. Other packed-tube foam generators are described in detail in "A mechanical foam-generator for use in laboratories", by J. F. Fry and R. J. French, J. Appl. Chem., 1, 425–429 (1951). The operation of the foam generating device is known to the skilled artisan.

In Example 1 the incoming air is adjusted to about 60 psig, either by regulating the supply or by air pressure regulators 3 and 9. In Example 1 the flow rate of the fluid is set to 0.23 l/min. as indicated by the oval gear flow meter 15. Any change in foam quality may be made by adjusting air and/or fluid flow rates while ensuring that pressures remain below 60 psig, the set-point for pressure relief valves 4 and 12.

C) Coating of the Tablets

The foam produced in step B) is applied to the tablets produced in step A) in a Hi-Coater (Vector Corporation, Marian, Iowa, USA). Foam is applied to the tablets while tumbling until an even coating is achieved. A glossy, uniform coating is achieved with an approximately 1 percent weight gain.

EXAMPLE 2

Placebo tablets are produced as in Example 1, step A). An aqueous dispersion of 5 weight percent of a powder composition in 95 weight percent of water is prepared. The powder composition comprises a hydroxypropyl methyl cellulose and is commercially available under the Trademark Opadry Pink (YS-1-1232) manufactured by Colorcon (West Point, Pa., USA). From the aqueous solution a foam is prepared and applied to the tablets as in Example 1, steps B) and C). A glossy, uniform coating is achieved with an approximately 0.75 percent weight gain.

What is claimed is:

1. A process for coating solid particles comprising the steps of
   a) contacting a gas with a fluid composition comprising i) from 0.01 to 30 weight percent of a polymer, ii) from 99.99 to 70 percent of a liquid diluent, based on the total weight of the polymer i) and the liquid diluent ii), to produce a foam, and
   b) contacting the produced foam with solid particles and agitating the particles to provide a coating on the solid particles,
   wherein the solid particles comprise a drug or the fluid composition comprises a drug or the solid particles and the fluid composition comprise a drug,
   wherein the polymer i) has a weight average molecular weight of at least 10,000 and is one or more polymers selected from the group consisting of cellulose ethers, cellulose esters, polyalkylene oxides, homo- and copolymers of vinyl alcohol, and homo- and copolymers of vinylpyrrolidone,
   wherein the liquid diluent is a monofunctional alcohol, alkene, alkane, halogenated alkene, halogenated alkane, ether, ester, a paraffin oil, an animal oil, a vegetable oil, or water, and
   wherein the amount of other additives, if present, is up to 25 weight percent, based upon the total weight of the fluid composition.

2. The process of claim 1 wherein the solid particles have an average diameter of from 1 to 25 mm.

3. The process of claim 1 wherein tablets, granules, pellets, caplets, capsules, lozenges, suppositories, pessaries or implantable dosage forms are coated.

4. The process of claim 3 wherein the fluid composition comprises from 0.1 to 20 weight percent of the polymer i) and from 99.9 to 80 percent of the liquid diluent ii), based on the total weight of the polymer i) and the liquid diluent ii).

5. The process of claim 3 wherein the polymer i) is a $C_1$–$C_3$-alkyl cellulose, a $C_1$–$C_3$-alkyl hydroxy-$C_{1-3}$alkyl cellulose or a hydroxy-$C_{1-3}$-alkyl cellulose or a homo- or copolymers of vinylpyrrolidone or polyethylene oxide.

6. The process of claim 1 wherein the fluid composition comprises from 0.01 to 20 weight percent of the polymer i) and from 99.9 to 80 percent of the liquid diluent ii), based on the polymer i) and the liquid diluent ii).

7. The process of claim 6 wherein the polymer i) is a $C_1$–$C_3$-alkyl cellulose, a $C_1$–$C_3$-alkyl hydroxy $C_{1-3}$-alkyl cellulose or a hydroxy-$C_{1-3}$-alkyl cellulose or a homo- or copolymers of vinylpyrrolidone or polyethylene oxide.

8. The process of claim 7 wherein the polymer i) is a methyl cellulose with a methyl molar substitution $DS_{methoxyl}$ of from 0.05 to 3.0 or a hydroxypropyl methylcellulose with a $DS_{methoxyl}$ of from 0.5 to 3.0 or a $MD_{hydroxypropyxyl}$ of from 0.05 to 2.0.

9. The process of claim 8 wherein the foam is a water-based air foam.

10. The process of claim 7 wherein the foam is a water-based air foam.

11. The process of claim 1 wherein the polymer i) is a $C_1$–$C_3$-alkyl cellulose, a $C_1$–$C_3$-alkyl hydroxy-$C_{1-3}$-alkyl cellulose or a hydroxy-$C_{1-3}$-alkyl cellulose or a homo- or copolymers of vinylpyrrolidone or polyethylene oxide.

12. The process of claim 11 wherein the polymer i) is methyl cellulose with a methyl molar substitution $DS_{methoxyl}$ of from 0.5 to 3.0 and a $MS_{hydroxpropyxyl}$ of from 0.05 to 2.0.

13. The process of claim 1 wherein the fluid composition and the foam do not comprise a surfactant other than the polymer i).

14. The process of claim 1 wherein the foam is a water-based air foam.

15. The process of claim 1 wherein agitation of the particles in step b) is started before the foam is added to the particles and is continued during the foam addition.

16. The process of claim 1 wherein in step b) foam is added to continuously agitated solid particles.

17. A process for coating solid particles comprising the steps of
   a) contacting a gas with a fluid composition comprising i) from 0.01 to 30 weight percent of a polymer, ii) from 99.9 to 70 percent of a liquid diluent, based on the total weight of the polymer i) and the liquid diluent ii), to produce a foam, and
   b) contacting the produced foam with solid particles and agitating the particles to provide a coating on the solid particles,
   wherein the solid particles comprise a drug or the fluid composition comprises a drug or the solid particles and the fluid composition comprise a drug,
   wherein the polymer i) has a weight average molecular weight of at least 10,000 and is a cellulose ether or a cellulose ester and
   wherein the amount of other additives, if present, is up to 25 weight percent, based upon the total weight of the fluid composition.

* * * * *